US010276289B1

(12) United States Patent
Kirby et al.

(10) Patent No.: US 10,276,289 B1
(45) Date of Patent: Apr. 30, 2019

(54) ROTATING A PERMANENT MAGNET IN A POSITION DETECTION SYSTEM

(71) Applicant: OMMO Technologies, Inc., Plano, TX (US)

(72) Inventors: Jonah William Kirby, Lewisville, TX (US); Matthew Pickett, Nicasio, CA (US); Minjie Zheng, Plano, TX (US); Jonathan Feldkamp, Anderson, SC (US)

(73) Assignee: Ommo Technologies, Inc., Plano, TX (US)

( * ) Notice: Subject to any disclaimer, the term of this patent is extended or adjusted under 35 U.S.C. 154(b) by 0 days.

(21) Appl. No.: 15/996,055

(22) Filed: Jun. 1, 2018

(51) Int. Cl.
| | |
|---|---|
| *G01D 5/16* | (2006.01) |
| *H01F 7/02* | (2006.01) |
| *H01F 13/00* | (2006.01) |
| *G01B 7/00* | (2006.01) |
| *G01D 5/14* | (2006.01) |

(52) U.S. Cl.
CPC ........... *H01F 7/0273* (2013.01); *G01B 7/003* (2013.01); *G01D 5/145* (2013.01); *H01F 13/003* (2013.01)

(58) Field of Classification Search
CPC ............ G01D 5/145; G01D 5/16; G01D 5/14; G01D 5/147
USPC ..... 324/244, 205, 207.21, 207.22, 210, 213, 324/214, 219, 260, 262, 529, 750.12, 324/750.21, 754.17, 754.29
See application file for complete search history.

(56) References Cited

U.S. PATENT DOCUMENTS

| | | |
|---|---|---|
| 3,301,070 A | 1/1967 | Lapierre |
| 3,868,555 A | 2/1975 | Knowles |

(Continued)

FOREIGN PATENT DOCUMENTS

| | | |
|---|---|---|
| CN | 103412337 | 11/2013 |
| EP | 0928976 | 7/1999 |

(Continued)

OTHER PUBLICATIONS

USPTO, First Action Interview Pilot Program Pre-Interview Communication dated Aug. 30, 2018, in U.S. Appl. No. 15/436,967, 14 pgs.

(Continued)

*Primary Examiner* — Jermele M Hollington
*Assistant Examiner* — Taqi R Nasir
(74) *Attorney, Agent, or Firm* — Henry Patent Law Firm PLLC

(57) ABSTRACT

In a general aspect, a position detection system includes a magnetic field generator configured to generate a time-varying magnetic field. The magnetic field generator includes a carrier assembly that defines a first axis of rotation and comprises a permanent magnet having a center of mass. The magnetic field generator also includes a drive assembly that is coupled to the carrier assembly and configured to act on the carrier assembly to rotate the permanent magnet simultaneously about the first axis of rotation and a second axis of rotation. The second axis of rotation intersects the first axis of rotation at an intersection that is offset from the center of mass of the permanent magnet. The position detection system additionally includes a computer device configured to determine a position of a sensor based on magnetic field measurements obtained by the sensor in the time-varying magnetic field.

24 Claims, 8 Drawing Sheets

(56) References Cited

U.S. PATENT DOCUMENTS

| | | | |
|---|---|---|---|
| 5,153,546 A | 10/1992 | Laskaris | |
| 5,453,686 A | 9/1995 | Anderson | |
| 5,558,091 A | 9/1996 | Acker et al. | |
| 5,583,478 A | 12/1996 | Renzi | |
| 5,646,524 A | 7/1997 | Gilboa | |
| 6,049,327 A | 4/2000 | Walker et al. | |
| 6,073,043 A | 6/2000 | Schneider | |
| 6,140,813 A | 10/2000 | Sakanoue et al. | |
| 6,141,643 A | 10/2000 | Harmon | |
| 6,304,080 B1* | 10/2001 | Reznik | H02K 15/03 324/207.22 |
| 6,380,923 B1 | 4/2002 | Fukumoto et al. | |
| 6,400,139 B1 | 6/2002 | Khalfin et al. | |
| 6,420,640 B2 | 7/2002 | Koch | |
| 6,593,730 B2 | 7/2003 | Zapf | |
| 6,624,626 B2 | 9/2003 | Khalfin | |
| 6,686,881 B1 | 2/2004 | Lu et al. | |
| 6,747,632 B2 | 6/2004 | Howard | |
| 6,789,043 B1 | 9/2004 | Nelson et al. | |
| 6,830,337 B2 | 12/2004 | Angerpointner | |
| 6,861,945 B2 | 3/2005 | Kim et al. | |
| 6,967,596 B2 | 11/2005 | Nguyen | |
| 6,979,164 B2 | 12/2005 | Kramer | |
| 7,038,658 B2 | 5/2006 | Seki et al. | |
| 7,042,438 B2 | 5/2006 | McRae et al. | |
| 7,498,956 B2 | 3/2009 | Baier et al. | |
| 7,703,548 B2 | 4/2010 | Clark | |
| 7,798,253 B2 | 9/2010 | Schuh | |
| 7,859,249 B2 | 12/2010 | Zeller et al. | |
| 7,868,610 B2 | 1/2011 | Velinsky et al. | |
| 7,914,024 B2* | 3/2011 | Lohmuller | B60G 7/005 280/124.1 |
| 8,200,314 B2 | 6/2012 | Bladen et al. | |
| 8,208,192 B2 | 6/2012 | Keyworth et al. | |
| 8,279,091 B1 | 10/2012 | Tran et al. | |
| 8,381,718 B1 | 2/2013 | Luconi | |
| 8,425,438 B2 | 4/2013 | Fujimoto et al. | |
| 8,450,997 B2 | 5/2013 | Silverman | |
| 8,473,026 B2 | 6/2013 | Ferre et al. | |
| 8,490,717 B2 | 7/2013 | Bergstrom et al. | |
| 8,519,950 B2 | 8/2013 | Radivojevic et al. | |
| 8,525,627 B2 | 9/2013 | Higuchi | |
| 8,743,052 B1 | 6/2014 | Keller et al. | |
| 8,818,486 B2 | 8/2014 | Montag | |
| 8,903,414 B2 | 12/2014 | Marti et al. | |
| 8,955,458 B2 | 2/2015 | Salzmann et al. | |
| 9,002,675 B2 | 4/2015 | McIntyre et al. | |
| 9,182,456 B2 | 11/2015 | Shoemaker et al. | |
| 9,285,438 B2 | 3/2016 | Donovan et al. | |
| 9,551,561 B2 | 1/2017 | Kochanski | |
| 9,638,822 B2 | 5/2017 | Doany et al. | |
| 9,658,692 B1 | 5/2017 | Keyes et al. | |
| 9,823,092 B2 | 11/2017 | David et al. | |
| 10,151,606 B1 | 12/2018 | Memarzanjany et al. | |
| 2003/0146748 A1* | 8/2003 | Duncan | G01R 15/245 324/244.1 |
| 2004/0070392 A1* | 4/2004 | Hahn | G01D 5/04 324/207.22 |
| 2004/0107070 A1 | 6/2004 | Anderson et al. | |
| 2004/0263473 A1 | 12/2004 | Cho et al. | |
| 2006/0164086 A1 | 7/2006 | Kohlmuller | |
| 2006/0255795 A1 | 11/2006 | Higgins et al. | |
| 2006/0293593 A1 | 12/2006 | Govari et al. | |
| 2007/0132722 A1 | 6/2007 | Kim et al. | |
| 2008/0307025 A1 | 12/2008 | Licul | |
| 2009/0054077 A1 | 2/2009 | Gauthier et al. | |
| 2009/0146947 A1 | 6/2009 | Ng | |
| 2009/0156309 A1 | 6/2009 | Weston et al. | |
| 2009/0212979 A1 | 8/2009 | Catchings et al. | |
| 2009/0315547 A1* | 12/2009 | Abwa | G01R 33/02 324/244 |
| 2009/0322680 A1 | 12/2009 | Festa | |
| 2010/0090949 A1 | 4/2010 | Tianqiao et al. | |
| 2010/0156783 A1 | 6/2010 | Bajramovic | |
| 2010/0219813 A1* | 9/2010 | Ito | B60N 2/0232 324/207.22 |
| 2010/0231505 A1 | 9/2010 | Iwata | |
| 2011/0041834 A1 | 2/2011 | Liao | |
| 2012/0053448 A1 | 3/2012 | Griswold et al. | |
| 2012/0056805 A1 | 3/2012 | Bronner, Sr. et al. | |
| 2012/0084051 A1 | 4/2012 | Hackner et al. | |
| 2012/0319940 A1 | 12/2012 | Bress et al. | |
| 2013/0015844 A1* | 1/2013 | Bogos | G01D 5/24452 324/207.2 |
| 2013/0043863 A1 | 2/2013 | Ausserlechner et al. | |
| 2013/0238270 A1 | 9/2013 | Khalfin et al. | |
| 2013/0303878 A1 | 11/2013 | Nevo et al. | |
| 2014/0002063 A1 | 1/2014 | Ashe | |
| 2014/0055338 A1 | 2/2014 | Ryan | |
| 2014/0283599 A1 | 9/2014 | Kim et al. | |
| 2014/0371574 A1 | 12/2014 | Shusterman et al. | |
| 2015/0035743 A1 | 2/2015 | Rosener | |
| 2015/0061994 A1 | 3/2015 | Dai et al. | |
| 2015/0077336 A1 | 3/2015 | Elangovan | |
| 2015/0137796 A1* | 5/2015 | Ausserlechner | G01B 7/30 324/207.2 |
| 2015/0149104 A1 | 5/2015 | Baker et al. | |
| 2015/0185838 A1 | 7/2015 | Camacho-Perez et al. | |
| 2015/0185852 A1 | 7/2015 | Guo | |
| 2015/0198465 A1 | 7/2015 | El Alami | |
| 2015/0241976 A1 | 8/2015 | Zhao et al. | |
| 2015/0253847 A1 | 9/2015 | Harris et al. | |
| 2016/0011285 A1 | 1/2016 | Griswold et al. | |
| 2016/0223577 A1 | 8/2016 | Klosinski et al. | |
| 2017/0176623 A1 | 6/2017 | Appleby et al. | |
| 2018/0000554 A1 | 1/2018 | Paradis et al. | |

FOREIGN PATENT DOCUMENTS

| | | |
|---|---|---|
| EP | 1413820 | 4/2004 |
| WO | 2014/027243 | 2/2014 |
| WO | 2016/041088 | 3/2016 |
| WO | 2017/139871 | 8/2017 |

OTHER PUBLICATIONS

Fang, W., et al., "Optimization of Measuring Magnetic Fields for Position and Orientation Tracking", IEEE/ASME: Transactions on Mechatronics, vol. 16, No. 3, Jun. 2011, 9 pages.

Godinez, F. A, et al., "Note: Design of a novel rotating magnetic field device", Rev. Sci. Instrum. 83, 066109, 2012, 4 pages.

Raab, F. H, et al., "Magnetic Position and Orientation Tracking System", IEEE Transactions on Aerospace and Electronic Systems, vol. AES-15, No. 5, Sep. 1979, 10 pages.

Schlageter, V., et al., "A Magnetic Tracking System based on Highly Sensitive Integrated Hall Sensors", JSME International Journal, Series C, vol. 45, No. 4, 2002, 7 pages.

Stmicroelectronics, "Digital output magnetic sensor: ultra-low-power, high-performance 3-axis magnetometer", May 2015, 33 pages.

Chen, et al., "Finexus: Tracking Precise Motions of Multiple Fingertips Using Magnetic Sensing", Univ of Washington, UbiComp Lab, 2016, 11 pgs.

Paperno, E., et al., "A new method for magnetic position and orientation tracking", IEEE Transactions on Magnetics vol. 37, No. 4, Jul. 2001, 3 pages.

Popek, et al., "Localization Method for a Magnetic Capsule Endoscope Propelled by a Rotating Magnetic Dipole Field", IEEE International Conference on Robotics and Automation, Karlsruhe, Germany, May 2013, 6 pgs.

Schultze, et al., "Unambiguous position and orientation tracking using a rotating magnet", Journal of Applied Physics 114, 114502, 2013, 12 pgs.

Song, et al., "6-D Magnetic Localization and Orientation Method for an Annular Magnet Based on a Closed-Form Analytical Model", IEEE Transactions on Magnetics, vol. 50, No. 9, Sep. 2014, 11 pgs.

Song, et al., "An Electromagnetic Localization and Orientation Method Based on Rotating Magnetic Dipole", IEEE Transactions on Magnetics, Mar. 2013, 5 pgs.

(56) References Cited

OTHER PUBLICATIONS

Strachen, et al., "Accurate Indoor Navigation with Spinning Magnets", Dept of Electrical and Computer Engineering, Univ of Wisconsin-Madison, Apr. 2018, 2 pgs.
Wang, et al., "Analysis and visualization of rotation searching efficiency in two-round rotation based magnetic tracking", Dept. of Electronic Engineering, Fudan University, Shanghai, China, Nov. 18, 2015, 13 pgs.

* cited by examiner

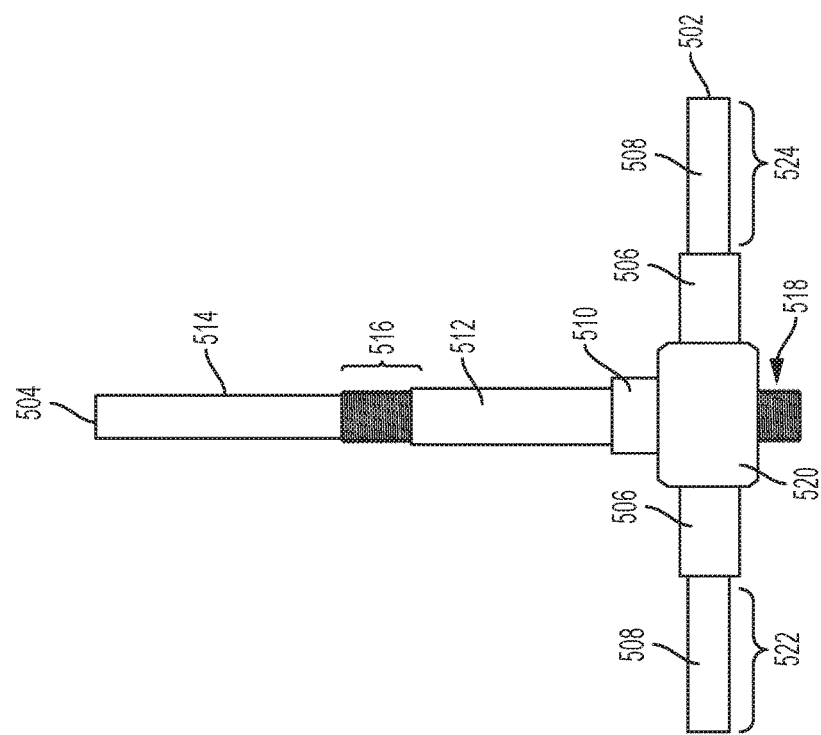

ROTATING A PERMANENT MAGNET IN A POSITION DETECTION SYSTEM

BACKGROUND

The following description relates to rotating a permanent magnet to generate a time-varying magnetic field, for example, in a position detection system.

Some existing systems can detect the position or movement of an object based on data collected by sensors. For example, vision-based positioning systems operate in the optical frequency range and utilize a line of sight between the image sensor and the object. As another example, sound-based positioning systems operate in an acoustic frequency range and utilize a propagation medium between the acoustic sensor and the object. As another example, inertial-based systems can use accelerometers or gyroscopes, for instance, to detect certain types of movement.

DESCRIPTION OF DRAWINGS

FIG. 5 is a schematic diagram of an example shaft assembly that includes a carrier shaft and a drive shaft;

DETAILED DESCRIPTION

In some aspects of what is described here, a position detection system includes a magnetic field generator configured to generate a time-varying magnetic field. The magnetic field generator includes a carrier assembly that defines a first axis of rotation and comprises a permanent magnet having a center of mass. The magnetic field generator also includes a drive assembly coupled to the carrier assembly and configured to act on the carrier assembly to rotate the permanent magnet simultaneously about the first axis of rotation and a second axis of rotation. The second axis of rotation intersects the first axis of rotation at an intersection that is offset from the center of mass of the permanent magnet. The position detection system additionally includes a computer device configured to determine a position of a sensor based on magnetic field measurements obtained by the sensor in the time-varying magnetic field.

The position detection system may compute and track, in real time, the position and orientation of a sensor (or an object coupled to the sensor) relative to the position detection system. The position detection system rotates a permanent magnet simultaneously about two axes, which may be orthogonal. The permanent magnet (e.g., its center of mass) is offset from an origin defined by an intersection of the two axes. The position detection system allows tracking the fine movements and positions of the sensor (or sensor-attached object) in a bounded, but mobile volume. Examples of such tracking include tracking the movements of hands and fingers for precise motion capture and novel forms of intuitive input (e.g., 3-dimensional interfaces, such as "augmented reality" or "virtual reality" interfaces), tracking the position of a scalpel in a medical procedure or training simulation, or tracking the position of pieces in games, such as checkers, chess, Warhammer™, and so forth. Other types of position detection and tracking are possible.

The position detection system is useful for many applications, including biomedical and healthcare applications (e.g., patient monitoring, surgical operations, remove operations, biopsy, etc.), virtual reality or augmented reality gaming applications, retail applications (e.g., product tracking, inventory management, employee training, etc.), military personnel, vehicular, and aircraft applications (e.g., personnel tracking, augmented reality or virtual reality combat field applications, etc.), robotics applications (e.g., remote tracking, robot manipulation, etc.), professional training applications (e.g., private, corporate, government, etc.), or any other application requiring position and motion tracking. The position detection system may also be capable of position and motion tracking in harsh natural environments.

Figure 1:
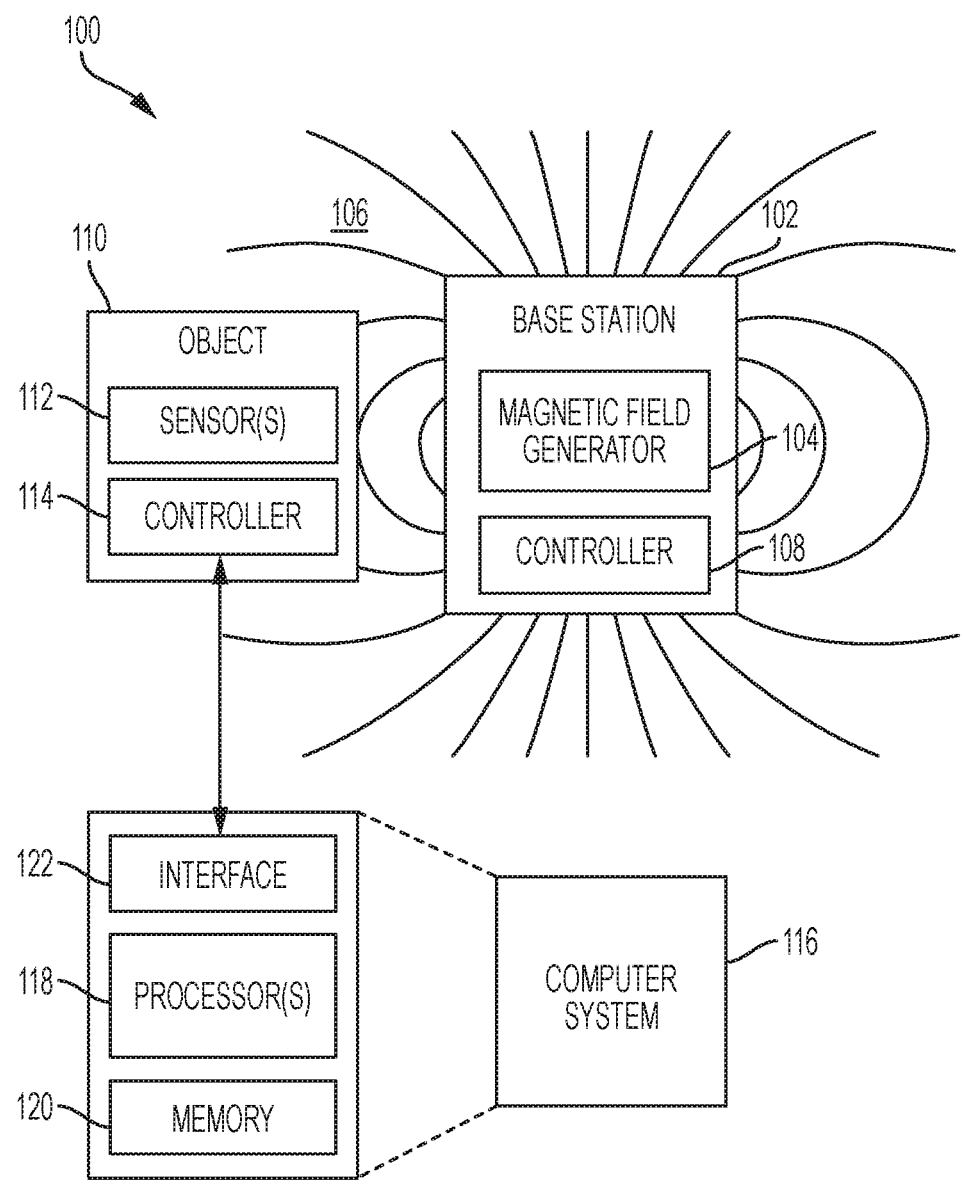
FIG. 1 is a schematic diagram of an example position detection system having a base station that includes a magnetic field generator.

Now referring to FIG. 1, a schematic diagram is presented of an example position detection system 100 having a base station 102 that includes a magnetic field generator 104. The magnetic field generator 104 is configured to produce a time-varying magnetic field 106 that can be used to detect the position of (or track) an object. The base station 102 also includes a base station controller 108 configured to regulate the time-varying magnetic field 106, which may include regulating a relative strength or orientation of the time-varying magnetic field and how the relative strength or orientation varies with time.

The example position detection system 100 also includes an object 110 coupled to a sensor 112. The example sensor 112 may be any type of sensor capable of measuring a magnetic field, including components thereof. For example, the sensor 112 may be a 3-axis magnetic field sensor, such as a magnetometer, a giant magnetoresistive (GMR) sensor, an anisotropic magnetoresistive (AMR) sensor, or a Hall-effect sensor. Although FIG. 1 depicts only one object and corresponding sensor, the position detection system 100 may have any number and combination of objects and sensors, including objects having multiple sensors. The object 110 additionally includes a sensor controller 114 in communication with the sensor 112. The example sensor controller 114 is operable to regulate the sensor 112 to take measurements of the time-varying magnetic field 106 at a position of the sensor 112, thereby producing sample data. The sensor controller 114 may also regulate the sensor 112 to take multiples of such measurements over time to produce corresponding sets of sample data.

The system 100 additionally includes an example computer system 116 having one or more processors 118 and one or more memories 120. The computer system 116 also includes an interface 122 in communication with the sensor controller 114. The example computer system 116 is operable to receive sample data from the sensor controller 114 and determine a position of the sensor 112 relative to the base station 102. In some cases, the computer system 116 may also send signals to the sensor controller 114 to regulate the acquisition of sample data from the sensor 112.

It will be understood that communication between the base station controller 108, the sensor controller 114, the computer system 116, or any combination thereof, may occur wirelessly. For example, the computer system 116 may communicate with the sensor controller 114 and the base station controller 108 via the ShockBurst™ and Enhanced ShockBurst™ protocols from Nordic Semiconductor. However, other examples of wireless protocols are possible, including Bluetooth, IrDA, Zigbee, Ultra Wide Band (IEEE 802.15), WLAN (IEEE 802.11), WiMAX (IEEE 802.16 & 802.20), and cellular (GMS, GPRS, EDGE, CMDA) protocols.

In some implementations, one or both of the object 110 and the base station 102 may include an inertial measurement unit (IMU), such as an accelerometer, a gyroscope, or a magnetometer. The inertial measurement unit may improve the accuracy and precision of a position determined by the example position detection system 100 (i.e., a position of the object 110). The inertial measurement unit may also smooth a pathway determined by the example position detection system 100 (e.g., during a motion of the object 110).

Figure 2:
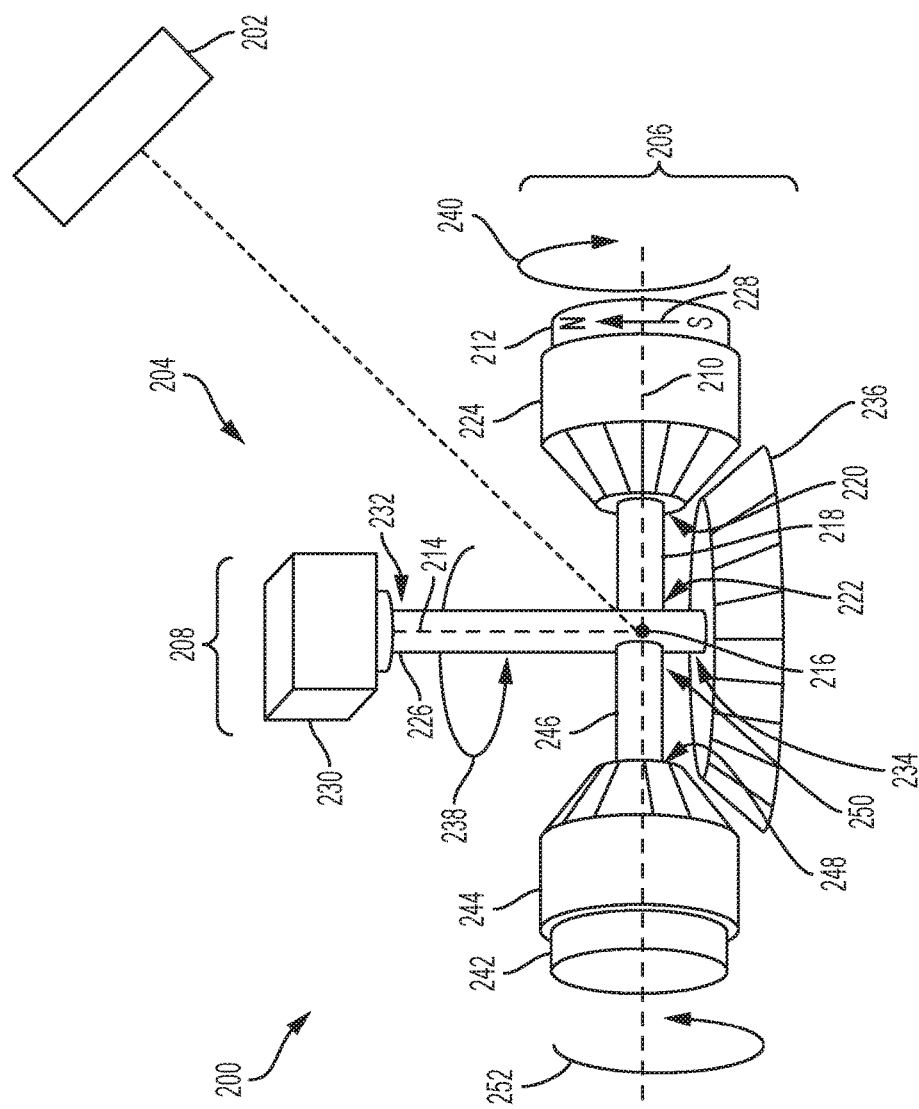
FIG. 2 is a schematic diagram of an example position detection system for determining a position of a sensor using a time-varying magnetic field.

Now referring to FIG. 2, a schematic diagram is presented of an example position detection system 200 for determining a position of a sensor 202 using a time-varying magnetic field. The sensor 202 is operable to measure a magnitude of the time-varying magnetic field, which changes as the position of the sensor 202 changes relative to the position detection system 200. The sensor 202 may be coupled to an object, thereby allowing the position detection system 200 to additionally determine a position of the object. For example, the sensor 202 may be an LIS3MDL sensor from ST Microelectronics, which is an ultra-low-power 3-axis MEMS magnetometer capable of high-performance. Other types of sensors may be used.

The example position detection system 200 includes a magnetic field generator 204 configured to generate the time-varying magnetic field. The magnetic field generator 204 includes a carrier assembly 206 and a drive assembly 208. The carrier assembly 206 defines a first axis of rotation 210 and includes a permanent magnet 212 having a center of mass. The drive assembly 208 is coupled to the carrier assembly 206 and is configured to act on the carrier assembly 206 to rotate the permanent magnet 212 simultaneously about the first axis of rotation 210 and a second axis of rotation 214. The second axis of rotation 214 intersects the first axis of rotation 210 at an intersection 216 that is offset from the center of mass of the permanent magnet 212. In some implementations, the second axis of rotation 214 is orthogonal to (i.e., perpendicular to) the first axis of rotation 210. In other implementations, the second axis of rotation 214 intersects the first axis of rotation 210 at a non-orthogonal angle.

The position detection system 200 also includes a computer device (e.g., the computer system 116 shown in FIG. 1 or another type of computer device) configured to determine the position of the sensor 202 based on magnetic field measurements obtained by the sensor 202 in the time-varying magnetic field. The computer device includes one or more processors and one or more memories to manipulate and store data representing the position of the sensor 202. The data may also represent an orientation of the sensor 202 relative to the position detection system 200. In some implementations, the computer device is in communication with a microprocessor coupled to an object (e.g., embedded). The object is coupled to the sensor 202 and may be a wearable object (e.g., a glove, a hat, etc.). In other implementations, the computer device is coupled directly to the object (e.g., embedded). In these implementations, the computer device may include one or more processors in communication with the sensor 202. The object may be a wearable object (e.g., a glove, a hat, etc.).

In some implementations, such as shown in FIG. 2, the carrier assembly 206 includes a carrier shaft extending along the first axis of rotation 210. More specifically, the example carrier assembly 206 includes a first carrier shaft 218 disposed along the first axis of rotation 210 and having a first end 220 and a second end 222. The permanent magnet 212 is coupled to a first bevel gear 224, which in turn, is coupled to the first end 220 of the first carrier shaft 218. This latter coupling may occur through a primary bearing (or bushing) that allows rotation of the first bevel gear 224 about the first carrier shaft 218. The second end 222 of the first carrier shaft 218 is coupled to a drive shaft 226 of the drive assembly 208. Such coupling may be a static coupling, i.e., the first carrier shaft 218 does not rotate about the first axis of rotation 210. Alternatively, the coupling may be a rotatable coupling, such as through a secondary bearing (or bushing).

The permanent magnet 212 may be coupled to the first bevel gear 224 such that a dipole magnetic field 228 of the permanent magnet 212 is oriented orthogonal to the first axis of rotation 210. In these instances, the dipole magnetic field 228 remains orthogonal to the first axis of rotation 210 as the permanent magnet 212 rotates about the first axis of rotation 210. If the second axis of rotation 214 is orthogonal to the first axis of rotation 210, as depicted by FIG. 2, the dipole magnetic field 228 also rotates in planes oriented parallel to the second axis of rotation 214 (i.e., a line normal to the planes intersects the second axis of rotation 214 at a perpendicular angle). However, other orientations of the permanent magnet 212, the first axis of rotation 210, and the second axis of rotation 214 are possible.

In some implementations, the drive assembly 208 includes a motor 230 configured to rotate the drive shaft 226 about the second axis of rotation 214. Because the drive shaft 226 is coupled to the carrier assembly 206, the motor 230 can rotate the carrier shaft (or the first carrier shaft 218) about the second axis of rotation 214. The drive shaft 226 is disposed along the second axis of rotation 214 and includes a first end 232 and a second end 234. The motor 230 (e.g., a brushless DC motor) is coupled to the first end 232 and a second bevel gear 236 is coupled to the second end 234. This coupling may include a drive bearing (or bushing).

As shown in FIG. 2, the first carrier shaft 218 and the drive shaft 226 define longitudinal axes that meet at the intersection 216. Moreover, the first carrier shaft 218 has a length that allows teeth of the first bevel gear 224 to engage those of the second bevel gear 236. This engagement allows the first bevel gear 224 to turn in response to the motor 230 rotating the drive shaft 226 about the second axis of rotation 214. As such, the first bevel gear 224 and the second bevel gear 236 may operate collectively to define a torque converter, which receives torque along the second axis of rotation 214 and converts a portion thereof to torque along the first axis of rotation 210 (i.e., to rotate the permanent magnet 212).

In some implementations, the magnetic field generator 204 includes a second sensor (not shown) configured to measure an angular position of the drive shaft 226 about the second axis of rotation 214. The second sensor may assist in determining a magnetization direction of the dipole magnetic field 228. For example, the second sensor may be an AMT20 Series absolute modular encoder from CUI, Inc. that is coupled to the drive shaft 226. The modular encoder may have a resolution of 0.010 degrees or lower (e.g., 0.088 degrees). However, the second sensor is not limited to an encoder. Other types of sensors are possible for the second sensor, including one or more Hall-effect sensors disposed at fixed locations on the magnetic field generator 204.

In operation, the drive assembly 208 rotates the drive shaft 226 about the second axis of rotation 214, as indicated by arrow 238. The motor 230 turns the drive shaft 226, which is coupled to the second bevel gear 236 via the drive bearing (or bushing). The drive bearing (or bushing) allows the drive shaft 226 to turn while the second bevel gear 236 remains stationary. Because the drive assembly 208 is coupled to the carrier assembly 206, the first carrier shaft 218 and the first bevel gear 224 rotate about the second axis of rotation 214 in an orbit-like manner as the drive shaft 226 turns. Contact between teeth of the first bevel gear 224 and those of the second bevel gear 236 cause the first bevel gear 224 to turn and thus rotate about the first axis of rotation 210. Arrow 240 indicates a representative direction of rotation for the first bevel gear 224.

Due to the permanent magnet 212 being coupled to the first bevel gear 224, the permanent magnet 212 rotates simultaneously about the first axis of rotation 210 and the second axis of rotation 214. Such simultaneous rotation allows the permanent magnet 212 to generate the time-varying magnetic field associated with the magnetic field generator 204. The sensor 202 measures the magnitude of the time-varying magnetic field, B(t), which may involve measuring magnitudes associated with one or more orthogonal components of the time-varying magnetic field (e.g., $B_x$, $B_y$, and $B_y$). The sensor 202 sends signals to the computer device representing measurements of the time-varying magnetic field. The second sensor (if present) measures the angular position of the drive shaft 226 about the second axis of rotation 214. The second sensor then sends signals to the computer device that represents the angular position of the drive shaft 226 at the time the sensor 202 measured the magnitude of the time-varying magnetic field. The computer device receives these signals to produce data corresponding to the position of the sensor 202. When received repeatedly, the signals may allow the computer device to track a motion of the sensor 202 over a period of time.

Figure 3:
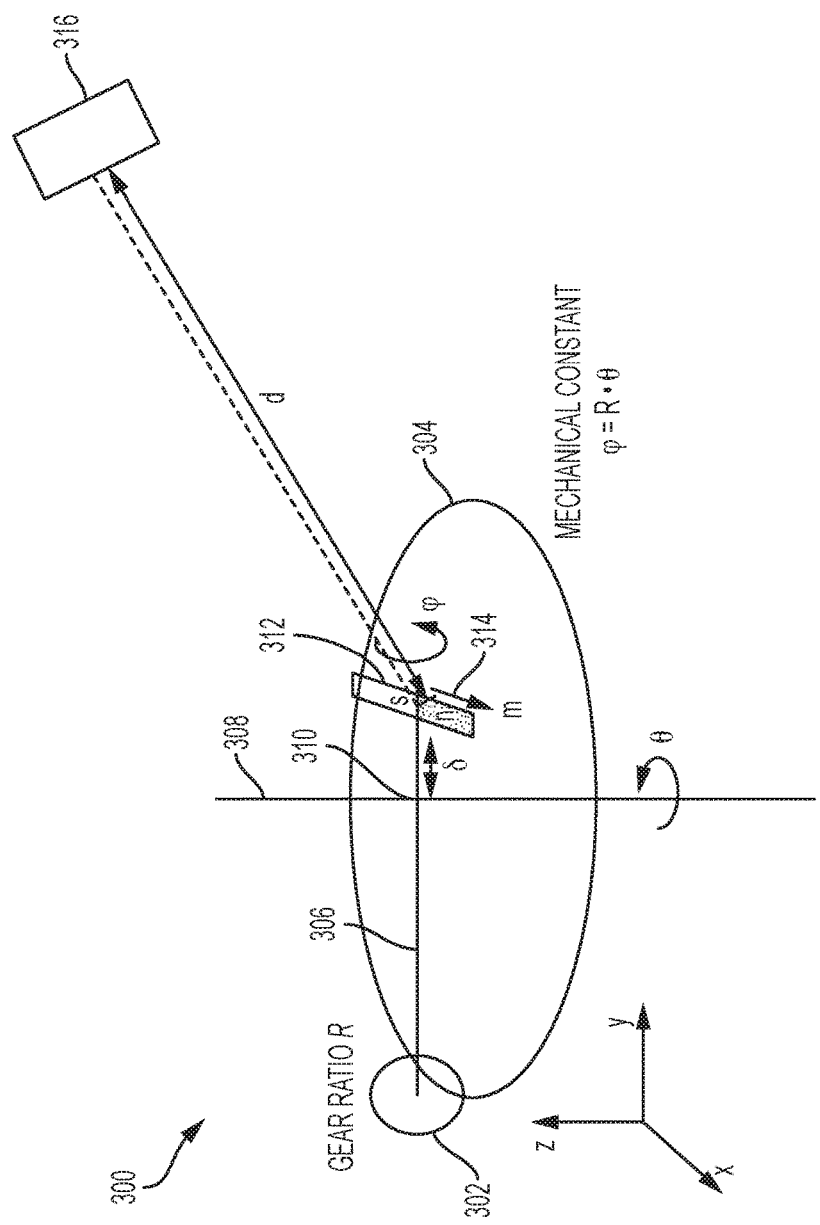
FIG. 3 is a schematic diagram of an example mathematical model of a magnetic field generator.

The magnetic field generator 204 rotates the permanent magnet 212 in a defined 3-dimensional motion that allows computation of a position in three dimensions using the sensor 202 (e.g., a single 3-axis magnetic sensor). In particular, a position of the sensor 202 may be computed within a tolerance of ±1 mm. FIG. 3 presents a schematic diagram of an example mathematical model of a magnetic field generator 300. The magnetic field generator 300 of FIG. 3 may be analogous to the magnetic field generator 204 of FIG. 2.

The magnetic field generator 300 includes a first gear 302 and a second gear 304 that collectively define a gear ratio, R. The first gear 302 has a first axis of rotation 306 that intersects with a second axis of rotation 308 associated with the second gear 304. The intersection corresponds to a reference origin 310 for the mathematical model. In this example, the gear ratio serves as a mechanical constant that fixes the rotation of the first gear 302 relative to the second (i.e., φ=R·θ). As such, the first gear 302 rotates through an angle φ that depends on a rotation of the second gear 304 through an angle θ as scaled by R. If the second gear 304 is stationary, the angle θ corresponds to an angular position of the first gear 302 about the second axis of rotation 308.

The magnetic field generator 300 also includes a permanent magnet 312 that produces a dipole magnetic field 314 with a magnetization direction, $\overline{m}$. The permanent magnet 312 is coupled to the first gear 302 and offset from the reference origin 310 by a magnitude, δ. Such coupling may occur via a shaft or other mechanical linkage disposed along the first axis of rotation 306. The first gear 302 and the permanent magnet 306 are capable of rotating about the first axis of rotation 306 and share an angular position represented by the angle φ. As such, the magnetization direction, $\overline{m}$, also has an angular position represented by the angle φ.

In the example shown in FIG. 3, the permanent magnet 312 moves through an even and stable sweep across 3-dimensional space, creating a trackable zone that has an associated time-varying magnetic field. Points within the trackable zone will experience a time-varying magnetic field vector that can be represented by $\vec{B}(t)=B_x(t)\hat{i}+B_y(t)\hat{j}+B_z(t)\hat{k}$. A sensor 316 may be disposed at a location near the magnetic field generator 300 to measure, in time, a magnetic field vector at the location. The offset (i.e., δ) of the permanent magnet 312 breaks a symmetry of magnetic field vectors measured at any arbitrary point. As such, a position of the sensor 316 can be uniquely determined within a full spherical volume around the magnetic field generator 300. This determination is aided by the simultaneous rotation of the permanent magnet 312 about the first axis of rotation 306 and the second axis of rotation 308. Such dual-axis rotation reduces the possible spatial coordinates of the sensor 316 to two sets of coordinates, one disposed polar opposite of the other.

By comparison, a single-axis rotation based on a magnitude of the magnetic field vector (i.e., $|\vec{B}|=\sqrt{B_x^2+B_y^2+B_z^2}$) would yield four possible spatial coordinates, one in each quadrant. In particular, with a single-axis rotation, the four possible spatial coordinates would correspond to [1] a real sensor position, [2] a polar opposite of the real sensor position (i.e., a straight line through the reference origin 310), [3] a reflection of the real position across a plane of rotation, and [4] a polar opposite of the reflection of the real position. The quadrants correspond to four respective regions defined by intersecting the plane of rotation with a plane perpendicular to the plane of rotation through the reference origin 310.

In some example cases, a motion of the permanent magnet 312 may be described by Equations (1)-(2):

$$\overline{\Delta} = R_z(\theta) \cdot \begin{bmatrix} 0 \\ \delta \\ 0 \end{bmatrix} = \delta \begin{bmatrix} -\sin\theta \\ \cos\theta \\ 0 \end{bmatrix} \quad (1)$$

$$\overline{m} = R_z(\theta) \cdot R_y(\varphi) \cdot \begin{bmatrix} 1 \\ 0 \\ 0 \end{bmatrix} = \delta \begin{bmatrix} \cos\theta\sin\varphi \\ \sin\theta\cos\varphi \\ -\sin\varphi \end{bmatrix} \quad (2)$$

In Equation 1, $\overline{\Delta}$ is a vector characterizing a center-of-gravity of the permanent magnet 312 relative to the reference origin 310, i.e., an offset of the center of gravity, and δ is a magnitude of the offset along the first axis of rotation 306. It will be appreciated that $\overline{\Delta}$ changes as the permanent magnet 312 rotates while δ is constant due to being set mechanically. In Equation 2, $\overline{m}$ is a magnetization direction of the permanent magnet 312 (or dipole magnetic field 228), and $R_z(\theta)$ and $R_y(\varphi)$ are defined according to respective Equations (3) and (4):

$$R_z(\theta) = \begin{bmatrix} \cos\theta & -\sin\theta & 0 \\ \sin\theta & \cos\theta & 0 \\ 0 & 0 & 1 \end{bmatrix} \quad (3)$$

$$R_y(\varphi) = \begin{bmatrix} \cos\varphi & 0 & \sin\varphi \\ 0 & 1 & 0 \\ -\sin\varphi & 0 & \cos\varphi \end{bmatrix}. \quad (4)$$

Equations (1)-(4) can be used (e.g., by a computer system) collectively with measurements from the sensor 316 to calculate a unique 3-dimensional position of the sensor 316 in a position detection system incorporating the magnetic field generator 300. The sensor 316 measures a magnetic field in each of three orthogonal directions (e.g., x, y, and z) to produce sampled data (e.g., $B_x$, $B_y$, and $B_y$). The measurements are referenced to a location of the sensor 316 and a single point in time. Simultaneously, the angle $\theta$ is measured, which corresponds to an angular position of the permanent magnet 312 about the second axis of rotation 308. The angle $\theta$ may be measured by a second sensor, such as the AMT20 Series absolute modular encoder described in relation to FIG. 2.

A computing device may pre-process the sampled data to remove DC bias from the measurement as well as interference from other magnetic sources. For example, the sampled data can be pre-processed to remove a DC bias that results from the Earth's magnetic field. The computing device may include a band-pass filter having a cut-off frequency closely-centered around a rotational frequency of the permanent magnet 312. The band-pass filter is operable to remove interference associated with a rotation of the permanent magnet 312 that would degrade a signal-to-noise ratio of the measurement.

The cut-off frequency of the band-pass filter may include one or both of the rotational frequencies associated with the first axis of rotation 306 and the second axis of rotation 308. In particular, the band-pass filter may remove low-frequency biases that are lower than a slower rotation and high-frequency biases that are greater than a faster rotation. For example, if the permanent magnet 312 rotates about the first axis of rotation 306 at 15 Hz and about the second axis of rotation 308 at 30 Hz, the cut-off frequency of the band-pass filter may be close to 15 Hz and 30 Hz. If the slower rotation and the faster rotation are too far apart in frequency for a single band-pass filter, multiple band-pass filters may be used.

In some cases, the computing device determines a magnetic field magnitude, B, for the sample data using the equation $B=\sqrt{B_x^2+B_y^2+B_z^2}$. The computing device may also determine the angle $\varphi$ from the measured angle $\theta$ using the gear ratio R (i.e., $\varphi=R\cdot\theta$). Equations (1)-(4) may then be used to determine the offset of the permanent magnet 312 (i.e., $\overline{\Delta}$) and its magnetization direction (i.e., $\overline{m}$). With the determined magnetic field magnitude (i.e., B) and magnetization direction (i.e., $\overline{m}$), the computing device may then reference a curve of magnetic field strength versus distance for the permanent magnet 312 to determine a distance, d, of the sensor 316 from the permanent magnet 312. The offset of the permanent magnet 312 (i.e., $\overline{\Delta}$) and the distance, d, of the sensor 316 from the permanent magnet 312 may define a sphere of radius, d, centered at $\overline{\Delta}$. The sphere represents all positions possible for the sensor 316 based on the sample data.

The position of the sensor 316 may be determined from an intersection of four such spheres. Due the configuration of the magnetic field generator 300, the spheres are non-concentric and the intersection of four such spheres is a unique 3-dimensional point. As such, given at least four sets of sample data, the computing device can determine four respective spheres having an intersection that corresponds to a unique 3-dimensional position of the sensor 316 relative to the origin 310. Increasing a number of sets of sample data may increase an accuracy and a precision of the position detection. Thus, sample data from the sensor 316 may be acquired at a sample rate. The sample rate may allow the computing device to compensate for a motion of the sensor 316, i.e., the sample rate may be sufficiently high that the sensor 316 is effectively motionless during an acquisition of four sets of sample data. For example, data may be sampled from the sensor 316 at a rate of 1 kHz to compensate for motion of the sensor 316.

Now referring back to FIG. 2, in some implementations the drive assembly 208 is configured to act on the carrier assembly 206 to rotate the permanent magnet 212 an integer number of full rotations about the first axis of rotation 210 for each individual full rotation of the permanent magnet 212 about the second axis of rotation 214. For example, the first bevel gear 224 and the second bevel gear 236 may have a gear ratio of 2:1 such that the permanent magnet 212 rotates twice about the first axis of rotation 210 for each rotation about the second axis of rotation 214. In some implementations, the drive assembly 208 is configured to act on the carrier assembly 206 to rotate the permanent magnet 212 an integer number of full rotations about the second axis of rotation 214 for each individual full rotation of the permanent magnet 212 about the first axis of rotation 210.

In the examples shown and described here, magnetic field generators can be configured to rotate a permanent magnet an integer (N) times about the first axis of rotation while rotating the permanent magnet another integer (M) times about the second axis of rotation, which corresponds to a rotation rate ratio of N:M. In other words, the rotation rate of the permanent magnet about the first axis and the rotation rate of the permanent magnet about the second axis define a rotation rate ratio of N:M. Generally, the values N and M can have any integer value. In some systems, N is larger than M, and therefore the permanent magnet rotates faster about the first axis than it does about the second axis. In some systems, M is larger than N, and therefore the permanent magnet rotates faster about the second axis than it does about the first axis. The rotation rate ratio may be defined based on a gear ratio or other mechanical properties, as an average ratio over many rotation cycles (e.g., over N rotations, M rotations, N*M rotations, etc.), as an instantaneous ratio, or otherwise.

In some cases, the permanent magnet is rotated at rotations speeds greater than 10 rotations per minute (RPM), greater than 100 RPM, or greater than 1000 RPM about one or both axes simultaneously. In some examples, the magnetic field generator system rotates the permanent magnet at a rate of up to 9000 rotations per minute (RPM) about the first axis of rotation and simultaneously rotates the permanent magnet at a rate of up to 3000 rotations per minute (RPM) about the second axis of rotation. In some examples, the magnetic field generator system rotates the permanent magnet at an average rate in the range of 2,400-4,500 rotations per minute (RPM) about the first axis of rotation and simultaneously rotates the permanent magnet at an average rate in the range of 1,200-1,500 rotations per minute (RPM) about the second axis of rotation. In some examples, the magnetic field generator system rotates the permanent magnet at an average rate of 1800 rotations per minute (RPM) about the first axis of rotation and simultaneously rotates the permanent magnet at an average rate of 900 rotations per minute (RPM) about the second axis of rotation. The magnetic field generator system may be configured to rotate the permanent magnet at another rate about one or both axes of rotation.

In some implementations, such as shown in FIG. 2, the carrier assembly 206 includes a non-magnetic counterweight 242 having a center of mass. The center of mass is offset from the intersection 216 along the first axis of rotation 210 and opposite the center of mass of the permanent magnet 212. The non-magnetic counterweight 242 may assist in stabilizing the carrier assembly 206 during rotation of the permanent magnet 212. However, the presence of the non-magnetic counterweight 242 is not necessary for the magnetic field generator 204 to generate a time-varying magnetic field for position tracking. In further implementations, the drive assembly 208 is configured to act on the carrier assembly 206 to simultaneously rotate the non-magnetic counterweight 242 about the first axis of rotation 210 and the second axis of rotation 214, and to simultaneously rotate the permanent magnet 212 about the first axis of rotation 210 and the second axis of rotation 214.

The non-magnetic counterweight 242 may be coupled to a third bevel gear 244. As shown in FIG. 2, the third bevel gear 244 is coupled to the drive shaft 226 via a second carrier shaft 246, which in some implementations, defines a single carrier shaft with the first carrier shaft 218. The second carrier shaft 246 assists the third bevel gear 244 in rotating about the first and second axes of rotation 210, 214. The second carrier shaft 246 is disposed along the first axis of rotation 210 and has a first end 248 coupled to the third bevel gear 244 and a second end 250 coupled to the drive shaft 226. Such coupling may occur through a bearing (or bushing) disposed at one or both of the first and second ends, 248, 250. The second end 250 may be disposed at (or proximate to) the intersection 216. The second carrier shaft 246 has a length that positions teeth of the third bevel gear 244 to engage those of the second bevel gear 236.

During operation, the second carrier shaft 246 and the third bevel gear 244 rotate about the second axis of rotation 214 as the motor 230 rotates the drive shaft 226. Contact between the second and third bevel gears 236, 244 causes the third bevel gear 244 to also rotate about the first axis of rotation 210. The non-magnetic counterweight 242 thus rotates simultaneously about the first and second axes of rotation 210, 214 by virtue of its coupling to the third bevel gear 244. This simultaneous rotation is similar to that associated with the permanent magnet 212, although the non-magnetic counterweight 242 rotates in a direction opposite that of the permanent magnet 212 (compare arrow 252 to arrow 240). Such counter rotation allows an Euler force(s) of the non-magnetic counterweight 242 to balance an Euler force(s) of the permanent magnet 212, thereby minimizing a gyroscopic effect. Without this counter rotation, devices incorporating the magnetic field generator may vibrate undesirably, e.g., a device may vibrate and "walk" across a surface that it is placed on. Moreover, users wearing such devices may be thrown off balance due to un- or poorly-compensated Euler forces.

In some implementations, such as shown in FIG. 2, the drive assembly 208 is configured to act on the carrier assembly 206 to simultaneously rotate the non-magnetic counterweight 242 and the permanent magnet 212 such that a gyroscopic effect of the permanent magnet 212 and a gyroscopic effect for the non-magnetic counterweight 242 offset each other. In certain implementations, the non-magnetic counterweight 242 may be of equal mass and moment of inertia as the permanent magnet 212. The center of mass of the non-magnetic counterweight 242 and the center of mass of the permanent magnet 212 may also be equidistant from the intersection 216, which serves as an origin. In these implementations, the carrier assembly 206 has an effective center of gravity on the first axis of rotation 210 that coincides with the intersection 216.

For example, the non-magnetic counterweight 242 may be implemented as a ring formed of stainless steel (e.g., Grade 304) and having an outer diameter of 37.3 mm, an inner diameter of 18 mm, and a thickness of 8.85 mm. The permanent magnet 212 may be a diametrically-magnetized ring formed of Nd—Fe—B alloy (e.g., grade N52) and having an outer diameter of 37.3 mm, an inner diameter of 18 mm, and a thickness of 9.5625 mm. With these features, the non-magnetic counterweight 242 and the permanent magnet 212 may each be offset 21.6 mm from the intersection 216 along the first axis of rotation 210 and opposite each other. However, other materials and corresponding dimensions may be used for the non-magnetic counterweight 242 and the permanent magnet 212. Moreover, dimensions of the non-magnetic counterweight 242 can be adjusted based on an actual material used to maintain equal mass and moment of inertia as the permanent magnet 212.

In the example shown in FIG. 2, the first carrier shaft 218 and the second carrier shaft 246 are aligned with each other and are orthogonal to the drive shaft 226; and accordingly, both are oriented parallel to the first axis of rotation 210 and perpendicular to the second axis of rotation 214. In some cases, one or both of the first carrier shaft 218 and the second carrier shaft 246 can have another orientation with respect to the drive shaft 226. For instance, the drive shaft 226, the first carrier shaft 218 and the second carrier shaft 246 can have a Y-shaped configuration in which the first carrier shaft 218 and the second carrier shaft 246 are not aligned with each other. As an example, the first carrier shaft 218 and the second carrier shaft 246 can each define an angle (e.g., 110 degrees, 120 degrees or otherwise) with respect to the drive shaft 226. In such cases, the permanent magnet 212 rotates about a first axis of rotation 210 that is not perpendicular to the second axis of rotation 214, and the non-magnetic counterweight 242 rotates about a third axis of rotation that is not perpendicular to the second axis of rotation 214. In such cases, the first, second and third axes of rotation can meet at the intersection 216.

Figure 4B:
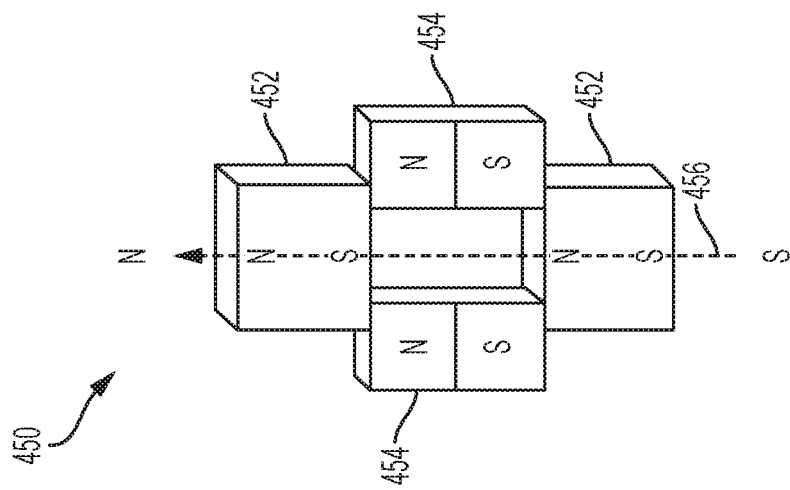
FIG. 4B is a schematic diagram of an example permanent magnet assembly having two square-shaped bar magnets and two rectangular-shaped bar magnets.
Figure 4A:
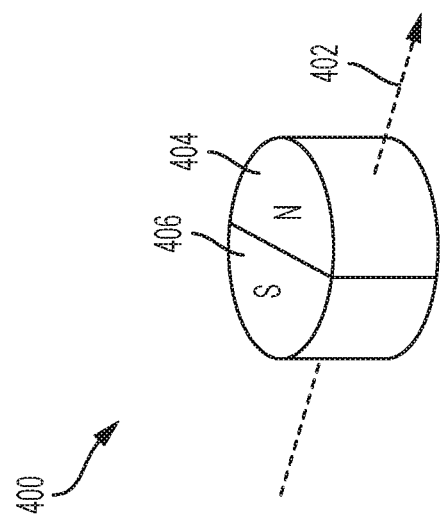
FIG. 4A is a schematic diagram of an example disk-shaped permanent magnet with an associated a dipole magnetic field.

The example permanent magnet 212 may include a single magnet that produces a dipole magnetic field. The single magnet may be a formed of any material capable of generating a persistent magnetic field after magnetization. Non-limiting examples of the material include an Nd—Fe—B alloy, a Sm—Co alloy, an Al—Ni—Co alloy, and a ferrite ceramic. The single magnet may be of any type of shape (e.g., bar, disk, ring, block, sphere, etc.). FIG. 4A presents a schematic diagram of an example disk-shaped permanent magnet 400 with an associated a dipole magnetic field 402. The disk-shaped magnet 400 has a "north" magnetic pole 404 disposed opposite of a "south" magnetic pole 406. The dipole magnetic field 402 is aligned parallel with a direction extending from the "south" magnetic pole 406 to the "north" magnetic pole 404. Although FIG. 4A presents the disk-shaped magnet 400 as being a single body, the permanent magnet 212 of FIG. 2 may have another shape or configuration.

In some implementations, the permanent magnet 212 is part of a permanent magnet assembly that includes one or more permanent magnets and produces a dipole magnetic field, i.e., the dipole magnetic field 228. In these implementations, the drive assembly 208 is configured to act on the carrier assembly 206 to rotate the dipole magnetic field 228 of the permanent magnet 212 simultaneously about the first axis of rotation 210 and the second axis of rotation 214. For example, FIG. 4B presents a schematic diagram of a permanent magnet assembly 450 having two square-shaped bar magnets 452 and two rectangular-shaped bar magnets 454. Each of the bar magnets 452, 454 has "north" and "south" magnetic poles defining individual magnetic dipoles that are collectively aligned in parallel to define a dipole magnetic field 456. It will be understood, however, that the permanent magnet assembly is not limited to square or rectangular shapes. Other shapes are possible (e.g., discs, cylinders, wedges, arc segments, stepped blocks, stepped disks, ellipsoids, etc.).

Now referring back to FIG. 2, the dipole magnetic field 228 may define a dipole axis of symmetry perpendicular to the first axis of rotation 210, and the drive assembly 208 is configured to act on the carrier assembly 206 to rotate the dipole axis of symmetry simultaneously about the first axis of rotation 210 and the second axis of rotation 214. The dipole magnetic field 228 may also define a center point that is offset from the intersection 216 between the first axis of rotation 210 and the second axis of rotation 214. The center point may be disposed on the first axis of rotation 210.

In the examples shown and discussed here, the center point of a dipole magnetic field is a point of symmetry of the dipole magnetic field. The point of symmetry may be found through a loop of electrical current that generates a dipole magnetic moment equivalent to that of the permanent magnet 212 (i.e., equivalent in magnitude and orientation). The loop of electrical current will converge onto the point of symmetry (e.g., the center point of the loop) as its dimensions are progressively reduced while keeping the magnitude of the dipole magnetic moment constant (i.e., by increasing a magnitude of the electric current).

Although FIG. 2 depicts the carrier shaft 218 and the drive shaft 226 as each having uniform diameters, the carrier shaft 218 and the drive shaft 226 may have diameters that vary over their respective lengths, which may assist in coupling to one or more bearings (or bushings). For instance, FIG. 5 presents a schematic diagram of an example shaft assembly 500 that includes a carrier shaft 502 and a drive shaft 504. The carrier shaft 502 and the drive shaft 504 of FIG. 5 may be analogous to the carrier shaft 218 and the drive shaft 226 of FIG. 2.

The example carrier shaft 502 has a first portion 506 with a first diameter (6 mm in the example shown) that steps down to a second portion 508 with a second, smaller diameter (4 mm in the example shown). The example drive shaft 504 has a first portion 510 with a first diameter (8 mm in the example shown) that steps down to a second portion 512 with a second, smaller diameter (6 mm in the example shown) that further steps down to a third portion 514 with a third, smaller diameter (4 mm in the example shown). A transition between the second and third portions 512, 514 of the drive shaft 504 includes a first threaded length 516, which may aid in coupling the drive shaft 504 to a motor. A second threaded length 518 at an end of the drive shaft 504 assists the drive shaft 504 in coupling to a union adapter 520.

The union adapter 520, in turn, is coupled to the carrier shaft 502 and orients the drive shaft 504 orthogonal to the carrier shaft 502.

Rotation of the drive shaft 504 about its longitudinal axis (i.e., rotation about a second axis of rotation) may be facilitated by bushings or bearings. In some implementations, two full ceramic bearings (e.g., type 686) may be used to secure rotation about the longitudinal axis of the drive shaft 504. The two full ceramic bearings may be disposed on the third portion 514 of the drive shaft 504. Similarly, rotation of a mechanical coupler, such as a gear or wheel, about a longitudinal axis of the carrier shaft 502 (i.e., rotation about a first axis of rotation) may also be facilitated by bushings or bearings. The mechanical coupler couples a permanent magnet to the bushings or bearings, which in turn, couple the mechanical coupler to the carrier shaft 502. During operation, the mechanical coupler and the permanent magnet rotate about (or on) the carrier shaft 502. The carrier shaft 502 is static relative to its longitudinal axis (i.e., no rotation). In some implementations, four full ceramic bearings (e.g., type 494) may be used to secure rotation of the mechanical coupler about (or on) the carrier shaft 502. The four full ceramic bearings (e.g., type 494) may be disposed on each end 522, 524 of the carrier shaft. Other types of bushings or bearings may be used to facilitate rotation of the drive shaft 504 and the mechanical coupler.

Although FIGS. 2 and 5 depict their respective drive shafts 226, 504 as being associated with a single driven element, a magnetic field generator can have more than one drive shaft. Each drive shaft can rotate independently of the others about the second axis of rotation. Moreover, although FIGS. 2 and 5 depict their respective carrier shafts 218, 502 as being associated with two non-driven elements (i.e., one for a permanent magnet and one for a non-magnetic counterweight), the magnetic field generator can have one or more non-driven carriers. Each non-driven carrier can rotate independently of the others about the first axis of rotation and uses the second axis of rotation as a fixed reference frame. The non-driven carriers may share a first axis of rotation in common, or alternatively, have respective axes of rotation that are independent of one another. Other configurations for the magnetic field generator are possible.

In the examples shown, the driven elements are mechanical assemblies or components that include a source of mechanical motion (e.g., a motor) to directly cause the mechanical assembly or component to move or rotate. By comparison, the non-driven elements are mechanical assemblies or components that lack a source of mechanical motion to cause its movement or rotation. For instance, a non-driven mechanical assembly may be configured to receive mechanical forces or torque to move or rotate from an external source of mechanical motion, i.e., indirectly. As such, the non-driven mechanical assembly or carrier may be coupled to a source of mechanical motion or a driven mechanical assembly incorporating such a source.

Figure 6:
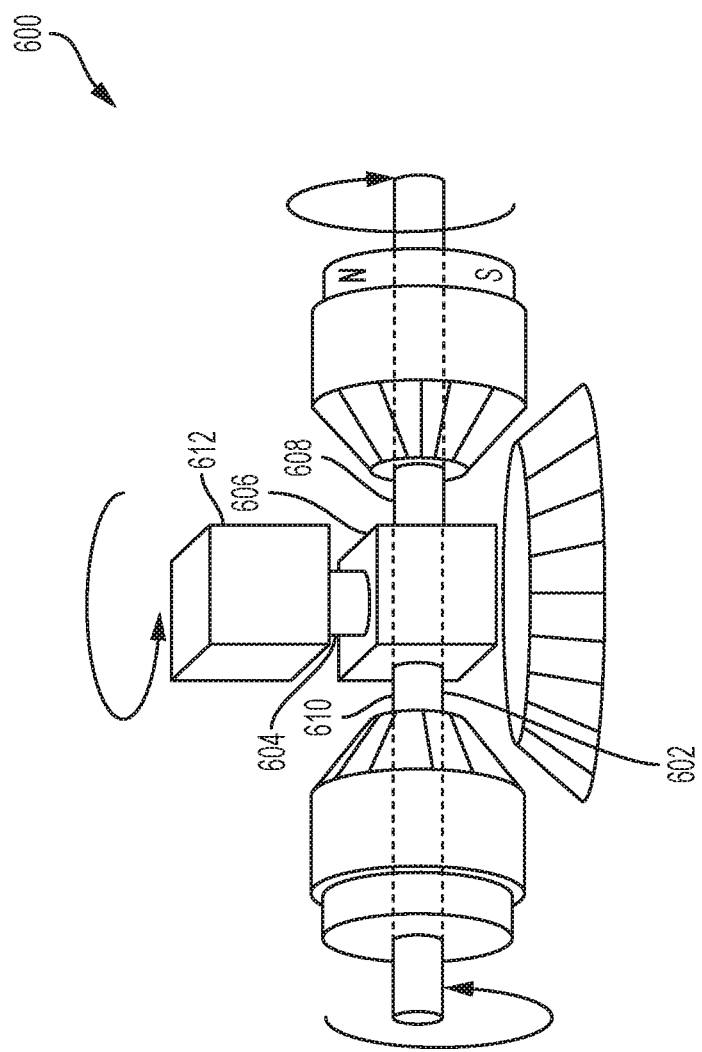
FIG. 6 is schematic diagram of an example magnetic field generator having two orthogonal shafts coupled via a coupling piece.

In some implementations, the magnetic field generator may include a coupling piece for joining a carrier shaft disposed along a first axis of rotation to a drive shaft disposed along a second axis of rotation. The first axis of rotation may be orthogonal to the second axis of rotation. FIG. 6 presents a schematic diagram of an example magnetic field generator 600 having two orthogonal shafts 602, 604 coupled via a coupling piece 606. The example coupling piece 606 is operable to transfer rotational energy of a drive shaft 604 directly to a carrier shaft 602, which in some instances, may be two independent shafts 608, 610. The rotational energy may be supplied by a motor 612.

Figure 7:
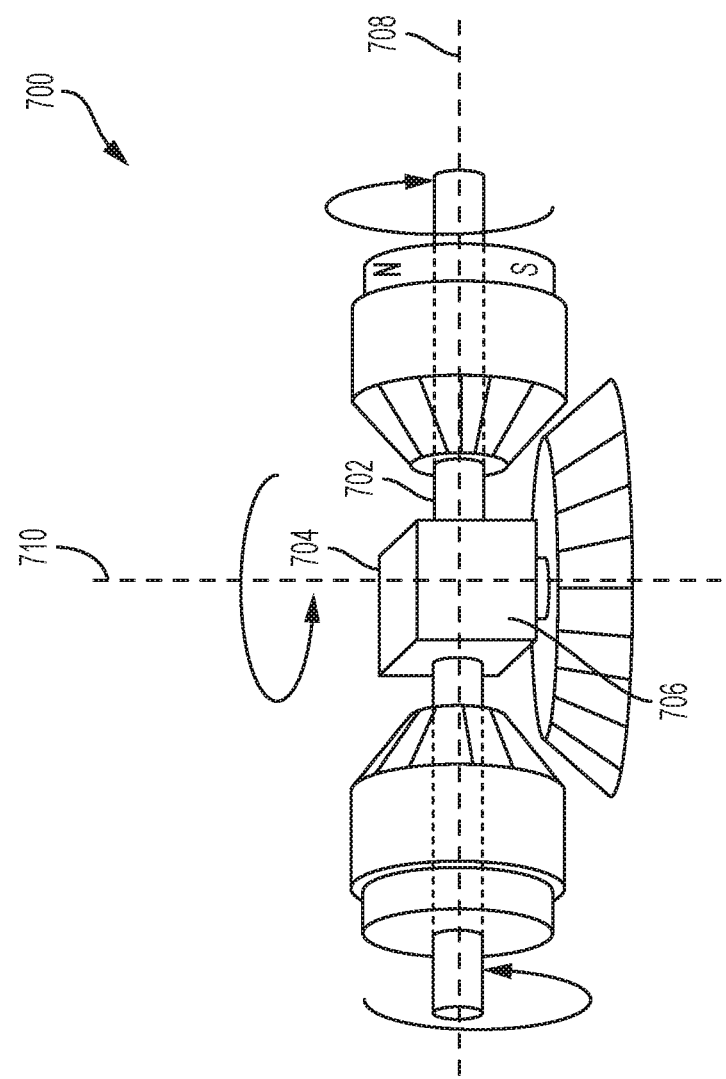
FIG. 7 is a schematic diagram of an example magnetic field generator having a drive mechanism incorporated along a single carrier shaft.

In other implementations, the magnetic field generator may include a drive mechanism that is incorporated along a carrier shaft. FIG. 7 presents a schematic diagram of an example magnetic field generator 700 having a drive mechanism 704 incorporated along a single carrier shaft 702. The drive mechanism 704 may be disposed at an intersection 706 of a first axis of rotation 708 and a second axis of rotation 710. The drive mechanism 704 is operable to rotate about the second axis of rotation 710, thereby inducing the components carried on the single carrier shaft 702 to rotate about the second axis of rotation 710.

Figure 8:
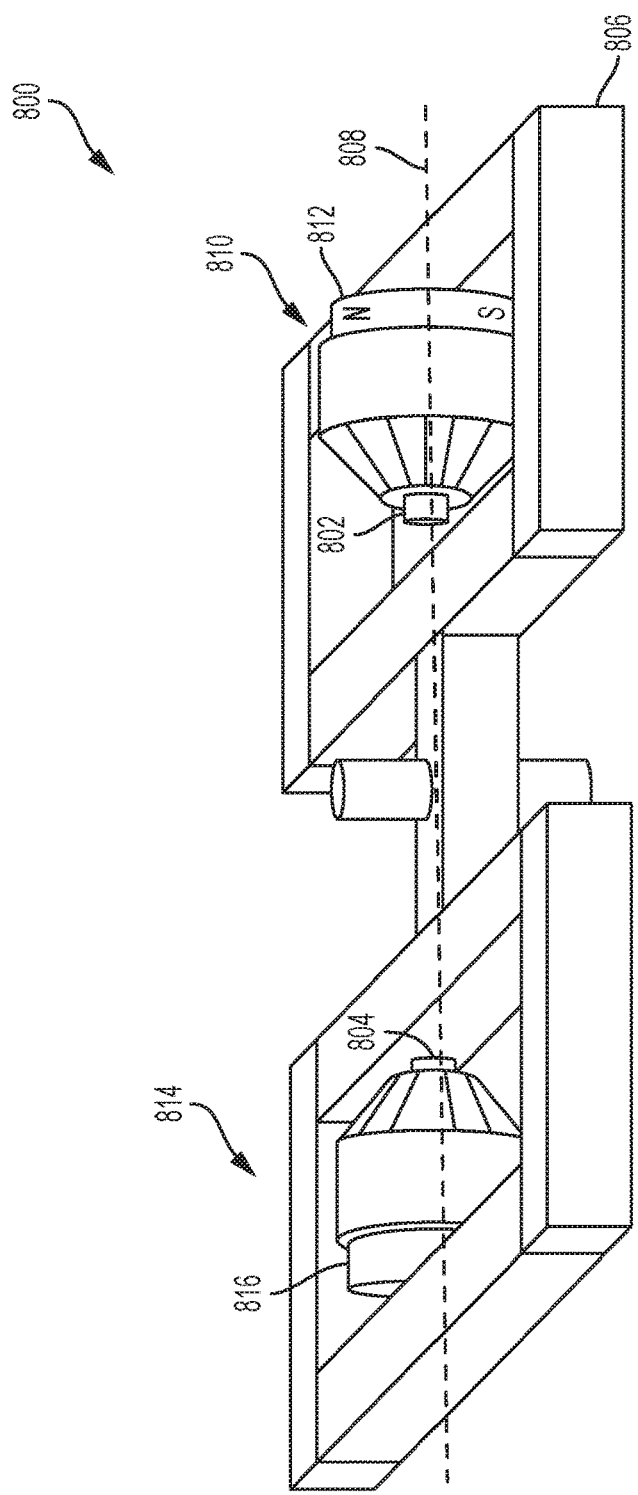
FIG. 8 is a schematic diagram of an example magnetic field generator having two carrier shafts coupled to a drive assembly.

In still other implementations, the magnetic field generator may include one or more carrier shafts coupled directly to a drive assembly without bearings or bushings. FIG. 8 presents a schematic diagram of an example magnetic field generator 800 having two carrier shafts 802, 804 coupled to a drive assembly 806. The carrier shafts 802, 804 correspond to a "broken back" design having a gap along a first axis of rotation 808. As such, the carrier shafts 802, 804 may be implemented as two independent shafts that function as separate non-driven carriers. In the example shown, one non-driven carrier 810 is associated with a permanent magnet 812 and the other non-driven carrier 814 is associated with a non-magnetic counterweight 816. In some instances, the carrier shafts 802, 804 are coupled to the drive assembly 806 through respective bearings (or bushings). The bearings allow the carrier shafts 802, 804 to rotate. In other instances, the carrier shafts 802, 804 each include bushings (or bearings) that allow components attached thereto (e.g., gears) to rotate on the carrier shafts 802, 804.

Now referring back to FIG. 2, the drive assembly 208 includes the motor 230, and the drive shaft 226 is coupled to the carrier assembly 206. The motor 230 is configured to rotate the drive shaft 226 about the second axis of rotation 214. In some implementations, the drive shaft 226 is configured to act on the carrier assembly 206 to rotate the carrier assembly 206 about the second axis of rotation 214. Moreover, the drive assembly 208 further includes a torque converter configured to act on the carrier assembly 206 to rotate the permanent magnet 212 about the first axis of rotation 210 while the carrier assembly 206 rotates about the second axis of rotation 214. The torque converter is capable of converting torque about the second axis of rotation 214 (or a portion thereof) into torque about the first axis of rotation 210. The torque converter may include gears, turbine blades, impellers, rubber wheels, or other components to effect such conversion. In the example shown in FIG. 2, the torque converter is depicted as including the second bevel gear 236.

In further implementations, the carrier assembly 206 includes the non-magnetic counterweight 242 and the torque converter is configured to act on the carrier assembly 206 to rotate the non-magnetic counterweight 242 about the first axis of rotation 210 while the carrier assembly 206 rotates about the second axis of rotation 214. In yet further implementations, the carrier assembly 206 comprises a first pinion gear (or the first bevel gear 224) associated with the permanent magnet 212 and a second pinion gear (or the third bevel gear 244) associated with non-magnetic counterweight 242. The torque converter includes a ring gear (or the second bevel gear 236) operatively coupled to the first and second pinion gears.

In some implementations, the drive assembly 208 includes a drive mechanism to power a rotation of the permanent magnet 212 simultaneously about the first axis of rotation 210 and the second axis of rotation 214. The drive mechanism may be singular or a plurality of drive mechanisms. Examples of the drive mechanism include motors, belt drives, coil actuators to spin small permanent magnets coupled to the drive shaft 226, and so forth. For example, the drive mechanism may be a 380 KV brushless DC motor attached to the drive shaft 226. The 380 KV brushless DC motor may be electrically coupled to a lithium polymer (LiPo) battery. During operation, the 380 KV brushless DC motor may draw about 200 mA in steady-state to drive rotational motion of the carrier assembly 206 and the drive assembly 208 in the magnetic field generator 204. The lithium polymer battery may be sufficiently small to allow the magnetic field generator 204 to be mobile. Moreover, one or more components of the carrier assembly 206, the drive assembly 208, or both, may be formed using a 3-dimensional printing system. In another example, the non-driven carriers 810, 814 of FIG. 8 may be coupled to the drive assembly 806 through respective motors, thus converting the non-driven carriers 810, 814 to driven carriers.

In some implementations, the drive assembly 208 includes a converter configured to transfer rotation about a driven axis to a non-driven axis. For example, the converter may transfer rotation from the second axis of rotation 214 to the first axis of rotation 210, as shown in FIG. 2. Alternatively, if the carrier assembly 206 includes a drive mechanism, the converter may transfer rotation from the first axis of rotation 210 to the second axis of rotation 214. The converter may be a torque converter and may include a bevel gear system, such as depicted in FIGS. 2 & 6-8. The bevel gear system may include a ring gear that is static in a fixed reference frame (e.g., the Earth) and two pinion gears. In FIG. 2, the second bevel gear 236 corresponds to the ring gear and the first bevel gear 224 and the third bevel gear 244 correspond to the two pinion gears. Each pinion gear may be coupled to a non-driven carrier shaft, such as the first carrier shaft 218 and the second carrier shaft 246 depicted in FIG. 2. Other types of gears are possible (e.g., worm gears). Moreover, other types of converters are possible.

In some examples, turbine blades or impellers may be used in place of pinion gears in the converter, such as the first and third bevel gears 224, 244. In these examples, the carrier assembly 206 is in contact with a fluid (e.g., water, oil, etc.), and possibly also the drive assembly 208. As the drive shaft 226 rotates about the second axis of rotation 214, the turbine blades or impellers experience drag from their contact with the fluid. Such drag transmits forces to the carrier assembly 206 that rotates the first carrier shaft 218 and the second carrier shaft 246 about the first axis of rotation 210. This rotation induces the permanent magnet 212 and the non-magnetic counterweight 242, respectively, to rotate. In other examples, rubber wheels may be used in place of gears in the converter. Friction between the rubber wheels and a surface will allow rotation about the second axis of rotation 214 to transfer to rotation about first axis of rotation 210 (or vice versa).

In some cases, the systems and techniques shown and described here can be used to rotate a permanent magnet to make use of the permanent magnet's magnetic field. Unlike a coil-generated magnetic field, rotating a permanent magnet typically requires orders of magnitude less power for comparable tracking ranges. As such, corresponding systems can be powered by small batteries for mobility, since the power is utilized primarily to overcome friction losses (e.g., aerodynamic drag, at bearings, between gears, etc.).

In some cases, the systems and techniques shown and described here can provide 3-dimensional rotation, and in particular, rotating a permanent magnet along two orthogonal axes simultaneously. In some examples, the 3-dimensional rotation does not require multiple drivers and can be achieved by a single driver. Moreover, the 3-dimensional rotation can be achieved via a converter that transfers rotation about one axis into rotation about an orthogonal axis. Such rotational motion may ensure that the permanent magnet's static magnetic field is getting a maximum sweep across a spherical zone around the magnet rotating mechanism, thus allowing sensors to measure the magnetic field and track their positions within the spherical zone.

In the examples shown and described, the permanent magnet is offset from an origin, which may correspond to a center of precession. Offsetting the permanent magnet from the center of precession during 3-dimensional rotation allows a reduction in symmetry that otherwise would exist in the magnetic field vector at polar opposite points. The offset thus allows the resolution of a unique 3D position in a full sphere around a position detection system by using only a single 3-axis magnetic sensor.

In some cases, the systems and techniques shown and described here can counter gyroscopic effects that result from rotations of the permanent magnet. For instance, the 3-dimensional rotation of the permanent magnet creates Euler forces that may cause instability and vibrations. By rotating a counterweight of similar angular momentum and mass in an opposing 3-dimensional rotation, the system maintains stability and is capable of being worn or deployed in another manner.

In some cases, the systems and techniques shown and described here can allow for notably reduced power consumption compared to conventional approaches. For instance, unlike coil-generated magnetic fields, which need to be maintained by high electrical current, the permanent magnet provides a constant magnetic field that requires no power to sustain. Moreover, the power required to maintain steady-state rotation is low as it only has to overcome the minimal frictional losses of the system, thus providing a significant power draw advantage.

In some cases, a motion detection system is not negatively impacted by occlusions in the magnetic field of the permanent magnet. The magnetic field, also known as a quasi-static magnetic field, may penetrate through virtually all matter, including human bodies, and is only re-routed by surface area of a ferromagnetic material. Due to this characteristic, sensors of the position detection system can accurately detect a strength of the magnetic field regardless of environment.

In some cases, insensitivity to occlusions provides advantages over other types of position tracking solutions, such as those that employ cameras and lasers. For instance, such cameras and lasers cannot maintain their tracking capability if occlusion occurs within their respective lines of sight, and therefore multiple cameras and lasers would be needed at various positions and angles, making any resulting product cumbersome and expensive. Cameras and laser systems may also require certain lighting conditions, whereas motion tracking with a time-varying magnetic field does not depend on lighting conditions.

In some cases, the systems and techniques shown and described here can determine a position of a sensor (or object attached to the sensor) with millimeter precision. Position detection with such precision can be computed for each sensor as the system powers on from an off state, even with no motion from the sensor. This ability offers an additional capability over tracking solutions that employ inertial measurement units (IMU) that calculate displacement by double integrating an acceleration measurement. Inertial measurement units typically have a quadratic error in displacement calculation from acceleration. They also have drift issues, where a calculation error continues to accumulate in random directions due to sensor noise, causing tracking to drift in those directions even when the sensor is stationary. Moreover, inertial measurement units typically start from a known initial position and recalibrate their positions from another source to counter drifting.

In some cases, the systems and techniques shown and described here can be less expensive than some conventional solutions. For instance, in some cases, the internal components may be readily manufactured or inexpensive to procure. Moreover, the low cost of internal components and their manufacture can be ideal for mass deployment in a commercial market. In some cases, a position detection system can be configured such that a user can easily afford and wear the system with them for mobile usage, and low power draw may allow the system to operate for multiple hours on small battery packs.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer storage medium for execution by, or to control the operation of, data-processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

Some of the operations described in this specification can be implemented as operations performed by a data processing apparatus on data stored on one or more computer-readable storage devices or received from other sources.

The term "data-processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read-only memory or a random-access memory or both. Elements of a computer can include a processor that performs actions in accordance with instructions, and one or more memory devices that store the instructions and data. A computer may also include, or be operatively coupled to receive data from or transfer data to, or both, one or more mass storage devices for storing data, e.g., magnetic disks, magneto optical disks, or optical disks. However, a computer need not have such devices. Moreover, a computer can be embedded in another device, e.g., a phone, an electronic appliance, a mobile audio or video player, a game console, a Global Positioning System (GPS) receiver, or a portable storage device (e.g., a universal serial bus (USB) flash drive). Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. In some cases, the processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

In a general aspect, a magnetic field generator generates a time-varying magnetic field.

In a first example, a position detection system includes a magnetic field generator configured to generate a time-varying magnetic field. The magnetic field generator includes a carrier assembly that defines a first axis of rotation and comprises a permanent magnet having a center of mass. The magnetic field generator includes a drive assembly coupled to the carrier assembly and configured to act on the carrier assembly to rotate the permanent magnet simultaneously about the first axis of rotation and a second axis of rotation. The second axis of rotation intersects the first axis of rotation at an intersection that is offset from the center of mass of the permanent magnet. The position detection system includes a computer device configured to determine a position of a sensor based on magnetic field measurements obtained by the sensor in the time-varying magnetic field.

Implementations of the first example may include one or more of the following features. The drive assembly can be configured to act on the carrier assembly to rotate the permanent magnet an integer number of full rotations about the first axis for each individual full rotation of the permanent magnet about the second axis. The drive assembly can be configured to act on the carrier assembly to rotate the permanent magnet an integer number of full rotations about the second axis for each individual full rotation of the permanent magnet about the first axis.

Implementations of the first example may include one or more of the following features. The carrier assembly can include a non-magnetic counterweight having a center of mass; the second axis can intersect the first axis at an intersection that is offset from (i) the center of mass of the permanent magnet, and (ii) the center of mass of the non-magnetic counterweight. The drive assembly can be configured to act on the carrier assembly to simultaneously (i) rotate the counterweight about the first axis and the second axis, and (ii) rotate the permanent magnet about the first axis and the second axis. The drive assembly can be configured to act on the carrier assembly to simultaneously rotate the non-magnetic counterweight and the permanent magnet such that a gyroscopic effect of the permanent magnet and a gyroscopic effect of the non-magnetic counterweight offset each other.

Implementations of the first example may include one or more of the following features. The permanent magnet can be part of a permanent magnet assembly that includes one or more permanent magnets and produces a dipole magnetic field. The drive assembly can be configured to act on the carrier assembly to rotate the dipole magnetic field simultaneously about the first axis and the second axis. The dipole magnetic field can define a dipole axis of symmetry perpendicular to the first axis, and the drive assembly can be configured to act on the carrier assembly to rotate the dipole axis of symmetry simultaneously about the first axis and the second axis. The dipole magnetic field can define a center point that is offset from the intersection between the first axis and the second axis.

Implementations of the first example may include one or more of the following features. The drive assembly can include a motor and a drive shaft coupled to the carrier assembly, and the motor can be configured to rotate the drive shaft about the second axis. The drive shaft can be configured to act on the carrier assembly to rotate the carrier assembly about the second axis, and the drive assembly can include a torque converter configured to act on the carrier assembly to rotate the permanent magnet about the first axis while the carrier assembly rotates about the second axis. The carrier assembly can include a non-magnetic counterweight, and the torque converter can be configured to act on the carrier assembly to rotate the non-magnetic counterweight about the first axis while the carrier assembly rotates about the second axis. The carrier assembly can include a first pinion gear associated with the permanent magnet and a second pinion gear associated with non-magnetic counterweight, and the torque converter can include a ring gear operatively coupled to the first and second pinion gears.

Implementations of the first example may include one or more of the following features. The carrier assembly can include a drive shaft extending along the first axis, and the drive assembly can include a motor configured to rotate the drive shaft about the first axis. The second axis can be perpendicular to the first axis.

In a second example, a method may include generating a time-varying magnetic field by operation of a magnetic field generator. The magnetic field generator generates the time-varying magnetic field by rotating a permanent magnet simultaneously about a first axis of rotation and a second axis of rotation. The second axis of rotation intersects the first axis of rotation at a location that is offset from a center of mass of the permanent magnet. The method also includes receiving magnetic field measurements obtained by a sensor in the time-varying magnetic field at a computer system. The method additionally includes determining a position of the sensor based on the magnetic field measurements by operation of the computer system.

Implementations of the second example may involve the magnetic field generator including a carrier assembly that defines the first axis of rotation and includes the permanent magnet. In these implementations, the magnetic field generator also includes a drive assembly that acts on the carrier assembly to rotate the permanent magnet simultaneously about the first axis of rotation and the second axis of rotation. In some implementations, the magnetic field generator generates the time-varying magnetic field by rotating the permanent magnet an integer number of multiple full rotations about the first axis of rotation for each individual full rotation of the permanent magnet about the second axis of rotation. In some implementations, the magnetic field generator generates the time-varying magnetic field by rotating the permanent magnet an integer number of multiple full rotations about the second axis of rotation for each individual full rotation of the permanent magnet about the first axis of rotation.

Implementations of the second example may also involve the magnetic field generator including a non-magnetic counterweight, and the magnetic field generator generates the time-varying magnetic field by simultaneously: [1] rotating the non-magnetic counterweight about the first axis of rotation and the second axis of rotation, and [2] rotating the permanent magnet about the first axis of rotation and the second axis of rotation. In further implementations, the magnetic field generator generates the time-varying magnetic field by simultaneously rotating the non-magnetic counterweight and the permanent magnet such that a gyroscopic effect of the permanent magnet and a gyroscopic effect of the non-magnetic counterweight offset each other.

Implementations of the second example may additionally have the permanent magnet as part of a permanent magnet assembly that includes one or more permanent magnets and produces a dipole magnetic field. In these implementations, the magnetic field generator generates the time-varying magnetic field by rotating the dipole magnetic field simultaneously about the first axis of rotation and the second axis of rotation. In further implementations, the dipole magnetic field defines a dipole axis of symmetry perpendicular to the first axis of rotation, and the magnetic field generator generates the time-varying magnetic field by rotating the dipole axis of symmetry simultaneously about the first axis of rotation and the second axis of rotation. In such implementations, the dipole magnetic field defines a center point that is offset from the intersection between the first axis of rotation and the second axis of rotation.

In certain implementations of the second example, the magnetic field generator generates the time-varying magnetic field by rotating the permanent magnet simultaneously: [1] about the first axis of rotation at a speed of 10 rotations per minute (RPM) or higher, 100 RPM or higher, or 1,000 RPM or higher, and [2] about the second axis of rotation at a speed of 10 rotations per minute (RPM) or higher, 100 RPM or higher, or 1,000 RPM or higher. In some implementations of the second example, the magnetic field generator generates the time-varying magnetic field by rotating the permanent magnet simultaneously about: [1] about the first axis of rotation at a speed of 30 rotations per minute (RPM) or higher, and [2] about the second axis of rotation at a speed of 30 rotations per minute (RPM) or higher.

In a third example, a magnetic field generator includes a carrier assembly that defines a first axis of rotation and comprises a permanent magnet having a center of mass. The magnetic field generator includes a drive assembly coupled to the carrier assembly and configured to act on the carrier assembly to rotate the permanent magnet simultaneously about the first axis of rotation and a second axis of rotation. The second axis of rotation intersects the first axis of rotation at an intersection that is offset from the center of mass of the permanent magnet.

The magnetic field generator of the third example may be used, for example, in a position detection system or in another type of system to generate a time-varying magnetic field. For instance, the permanent magnet can produce a field that is fixed with respect to the permanent magnet, and the time-varying attribute can arise from the rotation of the permanent magnet with respect to a given reference frame.

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of embodiments have been described. Nevertheless, it will be understood that various modifications can be made. Accordingly, other embodiments are within the scope of the following claims.

What is claimed is:

1. A position detection system comprising:
 a magnetic field generator configured to generate a time-varying magnetic field, the magnetic field generator comprising:
  a carrier assembly that defines a first axis of rotation and comprises a permanent magnet having a center of mass; and
  a drive assembly coupled to the carrier assembly and configured to act on the carrier assembly to rotate the permanent magnet simultaneously about the first axis of rotation and a second axis of rotation, the second axis of rotation intersecting the first axis of rotation at an intersection that is offset from the center of mass of the permanent magnet;
 a computer device configured to determine a position of a sensor based on magnetic field measurements obtained by the sensor in the time-varying magnetic field.

2. The position detection system of claim 1, wherein the drive assembly is configured to act on the carrier assembly to rotate the permanent magnet an integer number of full rotations about the first axis for each individual full rotation of the permanent magnet about the second axis.

3. The position detection system of claim 1, wherein the drive assembly is configured to act on the carrier assembly to rotate the permanent magnet an integer number of full rotations about the second axis for each individual full rotation of the permanent magnet about the first axis.

4. The position detection system of claim 1, wherein the carrier assembly further comprises a non-magnetic counterweight having a center of mass offset from the intersection along the first axis of rotation and opposite the center of mass of the permanent magnet.

5. The position detection system of claim 4, wherein the drive assembly is configured to act on the carrier assembly to simultaneously:
 rotate the non-magnetic counterweight about the first axis and the second axis, and
 rotate the permanent magnet about the first axis and the second axis.

6. The position detection system of claim 5, wherein the drive assembly is configured to act on the carrier assembly to simultaneously rotate the non-magnetic counterweight and the permanent magnet such that a gyroscopic effect of the permanent magnet and a gyroscopic effect of the non-magnetic counterweight offset each other.

7. The position detection system of claim 1, wherein the permanent magnet is part of a permanent magnet assembly that comprises one or more permanent magnets and produces a dipole magnetic field, and the drive assembly is configured to act on the carrier assembly to rotate the dipole magnetic field simultaneously about the first axis and the second axis.

8. The position detection system of claim 7, wherein the dipole magnetic field defines a dipole axis of symmetry perpendicular to the first axis, and the drive assembly is configured to act on the carrier assembly to rotate the dipole axis of symmetry simultaneously about the first axis and the second axis.

9. The position detection system of claim 7, wherein the dipole magnetic field defines a center point that is offset from the intersection between the first axis and the second axis.

10. The position detection system of claim 1, wherein the drive assembly comprises a motor and a drive shaft coupled to the carrier assembly, and the motor is configured to rotate the drive shaft about the second axis.

11. The position detection system of claim 10, wherein the drive shaft is configured to act on the carrier assembly to rotate the carrier assembly about the second axis, and the drive assembly further comprises a torque converter configured to act on the carrier assembly to rotate the permanent magnet about the first axis while the carrier assembly rotates about the second axis.

12. The position detection system of claim 11, wherein the carrier assembly further comprises a non-magnetic counterweight, and the torque converter is configured to act on the carrier assembly to rotate the non-magnetic counterweight about the first axis while the carrier assembly rotates about the second axis.

13. The position detection system of claim 12, wherein the carrier assembly comprises a first pinion gear associated with the permanent magnet and a second pinion gear associated with non-magnetic counterweight, and the torque converter comprises a ring gear operatively coupled to the first and second pinion gears.

14. The position detection system of claim 1, wherein the carrier assembly comprises a carrier shaft extending along the first axis, and the drive assembly comprises a motor configured to rotate the carrier shaft about the first axis.

15. The position detection system of claim 1, wherein the second axis is perpendicular to the first axis.

16. A method for position detection, comprising:
 generating a time-varying magnetic field by operation of a magnetic field generator, wherein the magnetic field generator generates the time-varying magnetic field by rotating a permanent magnet simultaneously about a first axis of rotation and a second axis of rotation, the second axis of rotation intersecting the first axis of rotation at a location that is offset from a center of mass of the permanent magnet;
 at a computer system, receiving magnetic field measurements obtained by a sensor in the time-varying magnetic field; and
 by operation of the computer system, determining a position of the sensor based on the magnetic field measurements.

17. The method of claim 16, wherein the magnetic field generator comprises:
 a carrier assembly that defines the first axis of rotation and comprises the permanent magnet; and
 a drive assembly that acts on the carrier assembly to rotate the permanent magnet simultaneously about the first axis of rotation and the second axis of rotation.

18. The method of claim 16, wherein the magnetic field generator generates the time-varying magnetic field by rotating the permanent magnet an integer number of multiple full rotations about the first axis for each individual full rotation of the permanent magnet about the second axis.

19. The method of claim 16, wherein the magnetic field generator generates the time-varying magnetic field by rotating the permanent magnet an integer number of multiple full rotations about the second axis for each individual full rotation of the permanent magnet about the first axis.

20. The method of claim 16, wherein the magnetic field generator further comprises a non-magnetic counterweight, and the magnetic field generator generates the time-varying magnetic field by simultaneously:

rotating the non-magnetic counterweight about the first axis and the second axis, and rotating the permanent magnet about the first axis and the second axis.

21. The method of claim 20, wherein the magnetic field generator generates the time-varying magnetic field by simultaneously rotating the non-magnetic counterweight and the permanent magnet such that a gyroscopic effect of the permanent magnet and a gyroscopic effect of the non-magnetic counterweight offset each other.

22. The method of claim 16, wherein the permanent magnet is part of a permanent magnet assembly that comprises one or more permanent magnets and produces a dipole magnetic field, and the magnetic field generator generates the time-varying magnetic field by rotating the dipole magnetic field simultaneously about the first axis and the second axis.

23. The method of claim 22, wherein:

the dipole magnetic field defines a dipole axis of symmetry perpendicular to the first axis, and the magnetic field generator generates the time-varying magnetic field by rotating the dipole axis of symmetry simultaneously about the first axis and the second axis, and the dipole magnetic field defines a center point that is offset from the intersection between the first axis and the second axis.

24. The method of claim 16, wherein the magnetic field generator generates the time-varying magnetic field by rotating the permanent magnet simultaneously:

about the first axis of rotation at a speed of 30 rotations per minute (RPM) or higher, and about the second axis of rotation at a speed of 30 rotations per minute (RPM) or higher.

* * * * *